(12) United States Patent
Mallo et al.

(10) Patent No.: US 7,033,600 B1
(45) Date of Patent: *Apr. 25, 2006

(54) INVERSE LATEX AND USE IN COSMETICS

(75) Inventors: Paul Mallo, Chatou (FR); Nelly Michel, Maisons-Alfort (FR)

(73) Assignee: Societe d'Exploitation de Produits Pour les Industries Chemiques SEPPIC, Paris Cedex (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 10/130,356

(22) PCT Filed: Nov. 19, 1999

(86) PCT No.: PCT/FR99/02850

§ 371 (c)(1),
(2), (4) Date: Sep. 26, 2002

(87) PCT Pub. No.: WO01/35922

PCT Pub. Date: May 25, 2001

(51) Int. Cl.
*A61K 8/02* (2006.01)
*A61K 8/18* (2006.01)
*A61K 9/00* (2006.01)
*A61Q 5/02* (2006.01)

(52) U.S. Cl. ............... 424/401; 424/70.1; 424/400; 510/119; 510/135; 514/937

(58) Field of Classification Search ........ 424/400, 424/401, 70.1; 514/937; 510/119, 135
See application file for complete search history.

(56) References Cited

U.S. PATENT DOCUMENTS

| 3,624,019 A | | 11/1971 | Anderson et al. |
|---|---|---|---|
| 4,873,078 A | | 10/1989 | Edmundson et al. |
| 5,124,376 A | * | 6/1992 | Clark, Jr. ............ 523/336 |
| 5,470,551 A | * | 11/1995 | Dubief et al. ......... 424/70.12 |
| 5,531,993 A | * | 7/1996 | Griat ............... 424/401 |
| 5,863,545 A | * | 1/1999 | Griat ............... 424/401 |
| 5,879,718 A | | 3/1999 | Sebillote-Arnaud |
| 5,885,563 A | | 3/1999 | Zegers |
| 6,013,270 A | * | 1/2000 | Hargraves et al. ...... 424/401 |
| 6,197,287 B1 | | 3/2001 | Mallo et al. |
| 6,375,958 B1 | * | 4/2002 | Cauwet et al. ........ 424/401 |
| 6,673,861 B1 | * | 1/2004 | Tabacchi et al. ....... 524/458 |

FOREIGN PATENT DOCUMENTS

| DE | 195 23 596 | 1/1997 |
|---|---|---|
| EP | 0 161 038 | 11/1985 |
| EP | 0 503 853 | 9/1992 |
| EP | 0 796 614 | 9/1997 |
| FR | 2 681 245 | 3/1993 |
| FR | 2 698 004 | 5/1994 |
| FR | 2 701 844 | 9/1994 |
| GB | 2 007 238 | 5/1979 |
| JP | 9-157130 | 6/1997 |

OTHER PUBLICATIONS

Emulsion Polymerization and Emulsion Polymers, John Wiley and Sons, 1997, pp. 726-734.

* cited by examiner

*Primary Examiner*—Sreeni Padmanabhan
*Assistant Examiner*—Marina Lamm
(74) *Attorney, Agent, or Firm*—Young & Thompson

(57) ABSTRACT

A cosmetic, dermopharmaceutical or pharmaceutical composition includes a composition containing an oil phase, an aqueous phase, a water-in-oil (W/O) emulsifier, an oil-in-water (O/W) emulsifier, in the form of a positive latex comprising 20 wt. % to 60 wt. %, and preferably 30 wt. % to 50 wt. %, of a branched or linear anion polyelectrolyte based on 2-methyl 2-[(1-oxo-2-propenyl)amino] 1-propanelsulphonic acid partly or completely salified, copolymerized with acrylamide, the organic solvent constituting the oil phase of the positive latex being isohexadecane.

11 Claims, No Drawings

INVERSE LATEX AND USE IN COSMETICS

The present patent application relates to thickening water-in-oil latices, to a process for preparing them and to their application as thickeners and/or emulsifiers for skincare products and haircare products or for the manufacture of cosmetic, dermopharmaceutical or pharmaceutical preparations.

Various thickeners exist and are already used for these purposes. Natural products such as guar gums or corn starch are known in particular, but the drawbacks of which are those inherent to natural products, such as price fluctuations, supply difficulties and inconsistent quality.

Synthetic polymers in powder form, mainly polyacrylic acids, are also widely used but have the drawback of requiring neutralization when they are used, since they only develop their viscosity from a pH above 6.5 and they are often difficult to dissolve.

Synthetic thickening polymers in the form of inverse latices, that is to say latices in which the continuous phase is an oil, also exist. These latices dissolve extremely quickly; the polymers contained in these inverse latices are usually acrylamide/alkali metal acrylate copolymers or acrylamide/sodium 2-acrylamido-2-methylpropanesulfonate copolymers; they are already neutralized and when they are dissolved in water, for example to a concentration of 1%, it is observed that the pH is generally above 6.

However, acrylamide/sodium acrylate copolymers do not develop any appreciable thickening properties when the pH is lowered below 6; on the other hand, the acrylamide/sodium 2-acrylamido-2-methylpropanesulfonate copolymers described in EP 0 503 853 retain an appreciable thickening capacity even at pH 4. However, inverse latices occasionally give rise to intolerance reactions on some types of sensitive skin; the Applicant thus became interested in investigating novel fluid inverse emulsions comprising the polymers mentioned above, which are better tolerated by the skin than those of the prior art, and in their use in the preparation of cosmetic, dermopharmaceutical or pharmaceutical compositions.

Thus, the Applicant prepared a novel composition comprising an oil phase, an aqueous phase, at least one emulsifier of water-in-oil (W/O) type, at least one emulsifier of oil-in-water (O/W) type, in the form of an inverse latex comprising from 20% to 60% by weight and preferably from 30% to 50% by weight of a branched or crosslinked anionic polyelectrolyte based on partially or totally salified 2-methyl-2-[(1-oxo-2-propenyl)amino]-1-propanesulfonic acid, copolymerized with acrylamide, the organic solvent constituting the oil phase being isohexadecane.

Isohexadecane, which is identified in Chemical Abstracts by the reference number RN=93685-80-4, is a mixture of $C_{12}$, $C_{16}$ and $C_{20}$ isoparaffins containing at least 97% of $C_{16}$ isoparaffins, among which the main constituent is 2,2,4,4,6,8,8-heptamethylnonane (RN=4390-04-9). It is sold in France by the company Bayer.

The anionic polyelectrolyte included in the inverse latex as defined above comprises, in molar proportions, from 30% to 50% of the sodium salt or the ammonium salt of 2-methyl-2-[(1-oxo-2-propenyl)amino]-1-propanesulfonic acid and from 50% to 70% acrylamide, and is especially crosslinked and/or branched with a diethylenic or polyethylenic compound in a molar proportion, expressed relative to the monomers used, of from 0.005% to 1% and preferably from 0.01% to 0.2%. The crosslinking agent and/or branching agent is chosen more particularly from ethylene glycol methacrylate, sodium diallyloxyacetate, ethylene glycol diacrylate, diallylurea, trimethylolpropane triacrylate and methylenebis(acrylamide).

The inverse latex as defined above generally contains from 4% to 10% by weight of emulsifiers. Its oil phase represents from 15% to 40% and preferably from 20% to 25% of its total weight. This latex may also contain one or more additives chosen especially from complexing agents, transfer agents and chain-limiting agents.

One subject of the invention is thus a cosmetic, dermopharmaceutical or pharmaceutical composition, characterized in that it comprises at least one thickening compound and at least one inverse latex as defined above.

The cosmetic, dermopharmaceutical or pharmaceutical composition defined above generally comprises from 0.1% to 10% and more particularly between 0.5% and 5% by weight of said inverse latex. It is especially in the form of a milk, a lotion, a gel, a cream, a soap, a bubble bath, a balm, a shampoo or a conditioner.

In general, said inverse latex can advantageously replace the products sold under the name Sepigel™ 305 or Sepigel™ 501 by the Applicant, in cosmetic, dermopharmaceutical or pharmaceutical compositions, since it also has good compatibility with the other excipients used for the preparation of formulations such as milks, lotions, creams, soaps, baths, balms, shampoos or conditioners. It can also be used with said Sepigel products.

In particular, the inverse latex is compatible with the concentrates described and claimed in the international publications WO 92/06778, WO 95/04592, WO 95/13863 and FR 2 734 496, and with the surfactants described in WO 93/08204.

The inverse latex is particularly compatible with Montanov™ 68, Montanov™ 82, Montanov™ 202 or Sepiperl™ N. It can also be used in emulsions of the type described and claimed in EP 0 629 396 and in cosmetically or physiologically acceptable aqueous dispersions with an organopolysiloxane compound chosen, for example, from those described in WO 93/05762 or in WO 93/21316. It can also be used to form cosmetically or physiologically acceptable aqueous gels of acidic pH, such as those described in WO 93/07856; it can also be used in combination with nonionic celluloses to form, for example, styling gels, such as those described in EP 0 684 024, or alternatively in combination with fatty acid esters of a sugar, to form compositions for treating the hair or the skin, such as those described in EP 0 603 019, or alternatively in shampoos or conditioners as described and claimed in WO 92/21316, or, lastly, in combination with an anionic homopolymer such as Carbopol™ to form hair-treatment products, such as those described in DE 195 23 596. It is also compatible with many active principles such as, for example, self-tanning agents, for instance dihydroxyacetone (DHA) or antiacne agents; it can thus be introduced into self-tanning compositions such as those claimed in EP 0 715 845, EP 0 604 249, EP 0 576 188 or in WO 93/07902. It is also compatible with N-acylated derivatives of amino acids, which allows it to be used in soothing compositions especially for sensitive skin, such as those described or claimed in WO 92/21318, WO 94/27561 or WO 98/09611. It is also compatible with glycolic acids, with lactic acid, with salicylic acid, retinoids, phenoxyethanol, sugars, glyceraldehyde, xanthans, fruit acids, and the various polyols used in the manufacture of cosmetic formulations.

A subject of the invention is thus also the use of an inverse latex as defined above, to prepare a cosmetic, dermopharmaceutical or pharmaceutical composition.

The object of the examples that follow is to illustrate the present invention without, however, limiting it. They show that the novel inverse latex does not irritate the skin and that its physical properties allow it to be used in the preparation of cosmetic, dermopharmaceutical or pharmaceutical compositions.

EXAMPLE 1

Preparation and Properties of the Inverse Latex

A Preparation Process

As described in European patent applications EP 0 186 361 and EP 0 503 853, a water-in-oil emulsion prepared from an aqueous solution adjusted to pH 5.8, comprising the monomers 2-acrylamido-2-methylpropane-sulfonic acid and acrylamide, and methylenebis(acrylamide), as crosslinking agent, and an organic solution comprising sorbitan oleate sold by the Applicant under the name Montane™ 80, and Witcamide™ 5115 (a partially esterified fatty acid N,N-dialkanolamide), dissolved in isohexadecane, is polymerized, followed by addition of ethoxylated (20 EO) sorbitan monooleate, sold by the Applicant under the name Montanox™ 80. The inverse latex obtained is characterized by the following viscosity measurements
(Temperature 20° C. Brookfield LVT):

| Dilution in water, as weight % | Viscosity in mPa · s |
|---|---|
| 0.5 | ≈1000 |
| 1.0 | ≈9000 |
| 1.5 | ≈30000 |
| 2.0 | ≈60000 |
| 2.5 | ≈80000 |
| 3.0 | ≈90000 |

B Properties a) Stabilizing Power with Respect to Fatty Phases

The inverse latex prepared in the above paragraph (composition 1) was used to prepare emulsions with different types of polar or apolar fatty substances, of plant or synthetic origin. The cream-gels obtained in the various cases are stable and of entirely uniform appearance. Their viscosity is given in the following table:

| Viscosity at 20° C., in mPa · s Brookfield LVT 6 rpm | Oil used for the fatty phase of the cream-gel (3% of composition 1; fatty phase: 20%) |
|---|---|
| ≈95000 | Jojoba oil |
| ≈95000 | Sweet almond oil |
| ≈90000 | Plant squalane |
| ≈80000 | Dimethicone |
| ≈82000 | Cyclomethicone |
| ≈92000 | Isononyl isononanoate |
| ≈95000 | Cetearyl octanoate |
| ≈92000 | $C_{12}$–$C_{15}$ benzoate |
| ≈90000 | Caprylic/capric TG | b) Heat Stability

A cream-gel comprising 3% of composition 1 and 20% cetearyl octanoate was prepared and the viscosity was measured. The results are as follows:

| | Brookfield LVT viscosity 6 rpm (in mPa · s) | |
|---|---|---|
| | At room temperature | At 50° C. |
| After 1 day | ≈90000 | |
| After 7 days | | ≈90000 |
| After 1 month | ≈87000 | ≈90000 | c) Effect of UV Radiation on the Stability

It is found that the gel prepared with composition 1 is very UV stable, since its viscosity did not change after 14 days of exposure.

d) Effect of the pH on the Viscosity

The viscosity of the cream-gel prepared with composition 1 is very pH-stable in the pH range from 3 to 8.

e) Comparative Tolerance Study

The inverse latex prepared according to paragraph A (composition 1) was compared with a composition (composition 2), as described in European patent application EP 0 503 853, comprising an oil phase, an aqueous phase, at least one emulsifier of water-in-oil (W/O) type, at least one emulsifier of oil-in-water (O/W) type, in the form of an inverse latex comprising from 20% to 60% by weight and preferably from 25% to 45% by weight of a branched or crosslinked anionic polyelectrolyte based on partially or totally salified 2-methyl-2-[(1-oxo-2-propenyl)amino]-1-propanesulfonic acid, copolymerized with acrylamide, characterized in that the organic solvent constituting the oil phase is Isopar™ M, sold by the company Exxon, which is a mixture of $C_{11}$–$C_{15}$ isoalkanes.

The skin tolerance was determined according to the "epicutaneous occlusion test" (patch test) on man. Aluminum cups 8 mm in diameter with a volume of 20 microliters were used, each cup allowing an area of 50 mm2 to be covered. They are mounted in pairs on an adhesive tape. The aqueous solution containing 3% or 5% of compositions 1 or 2 impregnates discs of blotting paper specially adapted for the cup/adhesive system. The system is applied to the skin (left subscapular region) of the subjects. Fourteen volunteers, with an average age of 29, were used as subjects. By way of reference, a 2% sodium lauryl sulfate solution, and also distilled water serving as a control, was also applied in the same way to each subject but on a different area of skin. 24 hours after the application, the cups are removed from the areas onto which they have been applied. The results are read 30 minutes and then 24 hours after the application. In order to examine whether or not the applied products are tolerated, the appearance of the following phenomena were taken into consideration: erythema, edema, vesicles, dry skin, rough skin, reflectivity of the skin. The percentage of total skin tolerance corresponds to the number of subjects presenting none of the phenomena mentioned above, relative to the total number of subjects, in the reading at 24 hours:

|  | Composition 1 | | Composition 2 | |
|---|---|---|---|---|
|  | 3% | 5% | 3% | 5% |
| Results at 24 hours (total tolerance) | 100% | 95% | 55% | 18% |

These results show, unexpectedly, that isohexadecane potentiates the skin tolerance of the copolymer. The following examples use composition 1 prepared in paragraph A.

EXAMPLE 2

Care Cream

| Cyclomethicone: | 10% |
|---|---|
| Composition 1: | 0.8% |
| Montanov ™ 68: | 2% |
| Stearyl alcohol: | 1% |
| Stearic alcohol: | 0.5% |
| Preserving agent: | 0.65% |
| Lysine: | 0.025% |
| EDTA (disodium salt): | 0.05% |
| Xanthan gum: | 0.2% |
| Glycerol: | 3% |
| Water: | qs 100% |

EXAMPLE 3

Care Cream

| Cyclomethicone: | 10% |
|---|---|
| Composition 1: | 0.8% |
| Montanov ™ 68: | 2% |
| Perfluoropolymethyl: |  |
| Isopropyl ether: | 0.5% |
| Stearyl alcohol: | 1% |
| Stearic alcohol: | 0.5% |
| Preserving agent: | 0.65% |
| Lysine: | 0.025% |
| EDTA (disodium salt): | 0.05% |
| Pemulen ™ TR: | 0.2% |
| Glycerol: | 3% |
| Water: | qs 100% |

EXAMPLE 4

Aftershave Balm

| FORMULA | | |
|---|---|---|
| A | Composition 1: | 1.5% |
|  | Water: | qs 100% |
| B | Micropearl ™ M 100: | 5.0% |
|  | Sepicide ™ CI: | 0.50% |
|  | Fragrance: | 0.20% |
|  | 95° ethanol: | 10.0% |

Procedure
Add B to A.

EXAMPLE 5

Satin Body Emulsion

| FORMULA | | |
|---|---|---|
| A | Simulsol ™ 165: | 5.0% |
|  | Lanol ™ 1688: | 8.50% |
|  | Karite butter: | 2% |
|  | Liquid paraffin: | 6.5% |
|  | Lanol ™ 14M: | 3% |
|  | Lanol ™ S: | 0.6% |
| B | Water: | 66.2% |
| C | Micropearl ™ M 100: | 5% |
| D | Composition 1: | 3% |
| E | Sepicide ™ CI: | 0.3% |
|  | Sepicide ™ HB: | 0.5% |
|  | Monteine ™ CA: | 1% |
|  | Fragrance: | 0.20% |
|  | Vitamin E acetate: | 0.20% |
|  | Sodium pyrrolidinonecarboxylate: | 1% (moisturizer) |

Procedure
Add C to B, emulsify B in A at 70° C. and then add D at 60° C., followed by E at 30° C.

EXAMPLE 6

Body Milk

| FORMULA | | |
|---|---|---|
| A | Simulsol ™ 165: | 5.0% |
|  | Lanol ™ 1688: | 12.0% |
|  | Lanol ™ 14M: | 2.0% |
|  | Cetyl alcohol: | 0.3% |
|  | Schercemol ™ OP: | 3% |
| B | Water: | qs 100% |
| C | Composition 1: | 0.35% |
| D | Sepicide ™ CI: | 0.2% |
|  | Sepicide ™ HB: | 0.5% |
|  | Fragrance: | 0.20% |

Procedure
Emulsify B in A at about 75° C.; add C at about 60° C., followed by D at about 30° C.

EXAMPLE 7

O/W Cream

| FORMULA | | | |
|---|---|---|---|
| A | Simulsol ™ 165: | 5.0% | |
|  | Lanol ™ 1688: | 20.0% | |
|  | Lanol ™ P: | 1.0% | (stabilizing additive) |
| B | Water: | qs 100% | |
| C | Composition 1: | 2.50% | |
| D | Sepicide ™ CI: | 0.20% | |
|  | Sepicide ™ HB: | 0.30% | |

Procedure

Introduce B into A at about 75° C.; add C at about 60° C., followed by D at 45° C.

EXAMPLE 8

Non-Greasy Antisun Gel

| | FORMULA | |
|---|---|---|
| A | Composition 1: | 3.00% |
| | Water: | 30% |
| B | Sepicide ™ CI: | 0.20% |
| | Sepicide ™ HB: | 0.30% |
| | Fragrance: | 0.10% |
| C | Colorant: | q.s. |
| | Water: | 30% |
| D | Micropearl ™ M 100: | 3.00% |
| | Water: | q.s. 100% |
| E | Silicone oil: | 2.0% |
| | Parsol ™ MCX: | 5.00% |

Procedure

Introduce B into A; add C, followed by D and then E.

EXAMPLE 9

Antisun Milk

| | FORMULA | |
|---|---|---|
| A | Sepiperl ™ N: | 3.0% |
| | Sesame oil: | 5.0% |
| | Parsol ™ MCX: | 5.0% |
| | λ-Carrageenan: | 0.10% |
| B | Water: | q.s. 100% |
| C | Composition 1: | 0.80% |
| D | Fragrance: | q.s. |
| | Preserving agent: | q.s. |

Procedure

Emulsify B in A at 75° C., then add C at about 60° C., followed by D at about 30° C., and adjust the pH if necessary.

EXAMPLE 10

Massage Gel

| | FORMULA | |
|---|---|---|
| A | Composition 1: | 3.5% |
| | Water: | 20.0% |
| B | Colorant: | 2 drops/100 g |
| | Water: | q.s. |
| C | Alcohol: | 10% |
| | Menthol: | 0.10% |
| D | Silicone oil: | 5.0% |

Procedure

Add B to A; then add C to the mixture, followed by D.

EXAMPLE 11

Massage Care Gel

| | FORMULA | |
|---|---|---|
| A | Composition 1: | 3.00% |
| | Water: | 30% |
| B | Sepicide ™ CI: | 0.20% |
| | Sepicide ™ HB: | 0.30% |
| | Fragrance: | 0.05% |
| C | Colorant: | q.s. |
| | Water: | q.s. 100% |
| D | Micropearl ™ SQL: | 5.00% |
| | Lanol ™ 1688: | 2% |

Procedure

Prepare A; add B, followed by C and then D.

EXAMPLE 12

Radiant-Effect Gel

| | FORMULA | |
|---|---|---|
| A | Composition 1: | 4% |
| | Water: | 30% |
| B | Elastine HPM: | 5.0% |
| C | Micropearl ™ M 100: | 3% |
| | Water: | 5% |
| D | Sepicide ™ CI: | 0.2% |
| | Sepicide ™ HB: | 0.3% |
| | Fragrance: | 0.06% |
| | 50% sodium pyrrolidinonecarboxylate: | 1% |
| | Water: | q.s. 100% |

Procedure

Prepare A; add B, followed by C and then D.

EXAMPLE 13

Body Milk

| | FORMULA | |
|---|---|---|
| A | Sepiperl ™ N: | 3.0% |
| | Glyceryl triheptanoate: | 10.0% |
| B | Water: | q.s. 100% |
| C | Composition 1: | 1.0% |
| D | Fragrance: | q.s. |
| | Preserving agent: | q.s. |

Procedure

Melt A at about 75° C. Emulsify B in A at 75° C. and then add C at about 60° C., followed by D.

EXAMPLE 14

Make-Up-Removing Emulsion Containing Sweet Almond Oil

| FORMULA | |
|---|---|
| Montanov ™ 68: | 5% |
| Sweet almond oil: | 5% |
| Water: | q.s. 100% |
| Composition 1: | 0.3% |
| Glycerol: | 5% |
| Preserving agent: | 0.2% |
| Fragrance: | 03% |

EXAMPLE 15

Moisturizing Cream for Greasy Skin

| FORMULA | |
|---|---|
| Mixture of laurylamino acids: | 0.1% to 5% |
| Magnesium potassium asparate: | 0.002% to 0.5% |
| Lanol ™ 99: | 2% |
| Sweet almond oil: | 0.5% |
| Water: | q.s. 100% |
| Composition 1: | 3% |
| Sepicide ™ HB: | 0.3% |
| Sepicide ™ CI: | 0.2% |
| Fragrance: | 0.4% |

EXAMPLE 16

Alcohol-Free, Soothing Aftershave Balm

| FORMULA | |
|---|---|
| Mixture of laurylamino acids: | 0.1% to 5% |
| Magnesium potassium aspartate: | 0.002% to 0.5% |
| Lanol ™ 99: | 2% |
| Sweet almond oil: | 0.5% |
| Water: | q.s. 100% |
| Composition 1: | 3% |
| Sepicide ™ HB: | 0.3% |
| Sepicide ™ CI: | 0.2% |
| Fragrance: | 0.4% |

EXAMPLE 17

Cream Containing AHAs for Sensitive Skin

| FORMULA | |
|---|---|
| Mixture of laurylamino acids: | 0.1% to 5% |
| Magnesium potassium aspartate: | 0.002% to 0.5% |
| Lanol ™ 99: | 2% |
| Montanov ™ 68: | 5.0% |
| Water: | q.s. 100% |

-continued

| FORMULA | |
|---|---|
| Composition 1: | 1.50% |
| Gluconic acid: | 1.50% |
| Triethylamine: | 0.9% |
| Sepicide ™ HB: | 0.3% |
| Sepicide ™ CI: | 0.2% |
| Fragrance: | 0.4% |

EXAMPLE 18

Aftersun Soothing Care Product

| FORMULA | |
|---|---|
| Mixture of laurylamino acids: | 0.1% to 5% |
| Magnesium potassium aspartate: | 0.002% to 0.5% |
| Lanol ™ 99: | 10.0% |
| Water: | q.s. 100% |
| Composition 1: | 2.50% |
| Sepicide ™ HB: | 0.3% |
| Sepicide ™ CI: | 0.2% |
| Fragrance: | 0.4% |
| Colorant: | 0.03% |

EXAMPLE 19

Make-Up-Removing Milk

| FORMULA | |
|---|---|
| Sepiperl ™ N: | 3% |
| Primol ™ 352: | 8.0% |
| Sweet almond oil: | 2% |
| Water: | q.s. 100% |
| Composition 1: | 0.8% |
| Preserving agent: | 0.2% |

EXAMPLE 20

Body Milk

| FORMULA | |
|---|---|
| Sepiperl ™ N: | 3.5% |
| Lanol ™ 37T: | 8.0% |
| Solagum ™ L: | 0.05% |
| Water: | qs. 100% |
| Benzophenone: | 2.0% |
| Dimethicone 350 cPs: | 0.05% |
| Composition 1: | 0.8% |
| Preserving agent: | 0.2% |
| Fragrance: | 0.4% |

EXAMPLE 21

Alkaline-pH Fluid Emulsion

| | |
|---|---|
| Marcol ™ 82: | 5.0% |
| NaOH: | 10.0% |
| Water: | q.s. 100% |
| Composition 1: | 1.5% |

EXAMPLE 22

Fluid Foundation

| FORMULA | |
|---|---|
| Simulsol ™ 165: | 5.0% |
| Lanol ™ 84D: | 8.0% |
| Lanol ™ 99: | 5.0% |
| Water: | q.s. 100% |
| Mineral fillers and pigments: | 10.0% |
| Composition 1: | 1.2% |
| Preserving agent: | 0.2% |
| Fragrance: | 0.4% |

EXAMPLE 23

Antisun Milk

| FORMULA | |
|---|---|
| Sepiperl ™ N: | 3.5% |
| Lanol ™ 37T: | 10.0% |
| Parsol NOX ™: | 5.0% |
| Eusolex ™ 4360: | 2.0% |
| Water: | q.s. 100% |
| Composition 1: | 1.8% |
| Preserving agent: | 0.2% |
| Fragrance: | 0.4% |

EXAMPLE 24

Gel for Around the Eyes

| | |
|---|---|
| Composition 1: | 2.0% |
| Fragrance: | 0.06% |
| Sodium pyrrolidinonecarboxylate: | 0.2% |
| Dow Corning ™ 245 Fluid: | 2.0% |
| Water: | q.s. 100% |

EXAMPLE 25

Leave-in Care Composition

| FORMULA | |
|---|---|
| Composition 1: | 1.5% |
| Fragrance: | q.s. |
| Preserving agent: | q.s. |
| Dow Corning ™ X2 8360: | 5.0% |
| Dow Corning ™ Q2 1401: | 15% |
| Water: | q.s. 100% |

EXAMPLE 26

Slimming Gel

| | |
|---|---|
| Composition 1: | 5% |
| Ethanol: | 30% |
| Menthol: | 0.1% |
| Caffeine: | 2.5% |
| Extract of butcher's-broom: | 2% |
| Extract of ivy: | 2% |
| Sepicide ™ HP: | 1% |
| Water: | q.s. 100% |

EXAMPLE 27

Alcohol-Free, Soothing Aftershave Balm

| FORMULA | | |
|---|---|---|
| A | Lipacide ™ PVB: | 1.0% |
| | Lanol ™ 99: | 2.0% |
| | Sweet almond oil: | 0.5% |
| B | Composition 1: | 3.5% |
| C | Water: | q.s. 100% |
| D | Fragrance: | 0.4% |
| | Sepicide ™ HB: | 0.4% |
| | Sepicide ™ CI: | 0.2% |

EXAMPLE 28

Refreshing Aftershave Gel

| FORMULA | | |
|---|---|---|
| A | Lipacide ™ PVB: | 0.5% |
| | Lanol ™ 99: | 5.0% |
| | Composition 1: | 2.5% |
| B | Water: | q.s. 100% |
| C | Micropearl ™ LM: | 0.5% |
| | Fragrance: | 0.2% |
| | Sepicide ™ HB: | 0.3% |
| | Sepicide ™ CI: | 0.2% |

EXAMPLE 29

Care Product for Greasy Skin

| FORMULA | | | |
|---|---|---|---|
| A | Micropearl ™ M310: | | 1.0% |
|   | Composition 1: | | 5.0% |
|   | Octyl isononanoate: | | 4.0% |
| B | Water: | q.s. | 100% |
| C | Sepicontrol ™ A5: | | 4.0% |
|   | Fragrance: | | 0.1% |
|   | Sepicide ™ HB: | | 0.3% |
|   | Sepicide ™ CI: | | 0.2% |
| D | Capigel ™ 98: | | 0.5% |
|   | Water: | | 10% |

EXAMPLE 30

Cream Containing AHAs

| FORMULA | | | |
|---|---|---|---|
| A | Montanov ™ 68: | | 5.0% |
|   | Lipacide ™ PVB: | | 1.05% |
|   | Lanol ™ 99: | | 10.0% |
| B | Water: | q.s. | 100% |
|   | Gluconic acid: | | 1.5% |
|   | TEA (triethylamine): | | 0.9% |
| C | Composition 1: | | 1.5% |
| D | Fragrance: | | 0.4% |
|   | Sepicide ™ HB: | | 0.2% |
|   | Sepicide ™ CI: | | 0.4% |

EXAMPLE 31

Non-Greasy Self-Tanning Product for the Face and the Body

| FORMULA | | | |
|---|---|---|---|
| A | Lanol ™ 2681: | | 3.0% |
|   | Composition 1: | | 2.5% |
| B | Water: | q.s. | 100% |
|   | Dihydroxyacetone: | | 3.0% |
| C | Fragrance: | | 0.2% |
|   | Sepicide ™ HB: | | 0.8% |
|   | NaOH (sodium hydroxide): | q.s. pH = | 5% |

EXAMPLE 32

Antisun Milk Containing Monoï de Tahiti

| FORMULA | | |
|---|---|---|
| A | Monoï de Tahiti: | 10% |
|   | Lipacide ™ PVB: | 0.5% |
|   | Composition 1: | 2.2% |

| FORMULA | | | |
|---|---|---|---|
| B | Water: | q.s. | 100% |
| C | Fragrance: | | 0.1% |
|   | Sepicide ™ HB: | | 0.3% |
|   | Sepicide ™ CI: | | 0.1% |
|   | Octyl methoxycinnamate: | | 4.0% |

EXAMPLE 33

Antisun Care Product for the Face

| FORMULA | | | |
|---|---|---|---|
| A | Cyclomethicone and dimethiconol: | | 4.0% |
|   | Composition 1: | | 3.5% |
| B | Water: | q.s. | 100% |
| C | Fragrance: | | 0.1% |
|   | Sepicide ™ HB: | | 0.3% |
|   | Sepicide ™ CI: | | 0.21% |
|   | Octyl methoxycinnamate: | | 5.0% |
|   | Titanium mica: | | 2.0% |
|   | Lactic acid: | q.s. pH = | 6.5 |

EXAMPLE 34

Self-Tanning Emulsion

| FORMULA | | | |
|---|---|---|---|
| A | Lanol ™ 99: | | 15% |
|   | Montanov ™ 68: | | 5.0% |
|   | Octyl para-methoxycinnamate: | | 3.0% |
| B | Water: | q.s. | 100% |
|   | Dihydroxyacetone: | | 5.0% |
|   | Monosodium phosphate: | | 0.2% |
| C | Composition 1: | | 0.5% |
| D | Fragrance: | | 0.3% |
|   | Sepicide ™ HB: | | 0.8% |
|   | NaOH: | q.s. pH = | 5. |

Montanov™ 68 (cetearyl glucoside) is a self-emulsifying composition as described in WO 92/06778, sold by the company SEPPIC.

Micropearl™ M100 is an ultrafine powder with a very soft feel sensation and a matt effect, sold by the company MATSUMO.

Sepicide™ CI, imidazolineurea, is a preserving agent sold by the company SEPPIC.

Pemulen™ TR is an acrylic polymer sold by GOODRICH.

Simulsol™ 165 is self-emulsifying glyceryl stearate, sold by the company SEPPIC.

Lanol™ 1688 is a non-greasy emollient ester sold by the company SEPPIC.

Lanol™ 14M and Lanol® S are consistency factors sold by the company SEPPIC.

Sepicide™ HB, which is a mixture of phenoxyethanol, methylparaben, ethylparaben, propylparaben and butylparaben, is a preserving agent sold by the company SEPPIC.

Monteine™ CA is a moisturizer sold by the company SEPPIC.

Schercemol™ OP is a non-greasy emollient ester.

Lanol™ P is a stabilizing additive sold by the company SEPPIC.

Parsol™ MCX is octyl para-methoxycinnamate, sold by the company Givaudan.

Sepiperl™ N is a pearlescent agent, sold by the company SEPPIC, based on a mixture of alkylpolyglucosides such as those described in WO 95/13863.

Micropearl™ SQL is a mixture of microparticles containing squalane, which is released under the action of massaging; it is sold by the company Matsumo.

Lanol™ 99 is isononyl isononanoate, sold by the company SEPPIC.

Lanol™ 37T is glyceryl triheptanoate, sold by the company SEPPIC.

Solagum™ L is a carrageenan sold by the company SEPPIC.

Marcol™ 82 is a liquid paraffin sold by the company ESSO.

Lanol™ 84D is dioctyl malate, sold by the company SEPPIC.

Parsol™ NOX is a sunscreen sold by the company Givaudan.

Eusolex™ 4360 is a sunscreen sold by the company Merck.

Dow Corning™ 245 Fluid is cyclomethicone, sold by the company Dow Corning.

Lipacide™ PVB is a palmitoylated wheat protein hydrolyzate sold by the company SEPPIC.

Micropearl™ LM is a mixture of squalane, poly(methyl methacrylate) and menthol, sold by the company SEPPIC.

Sepicontrol™ A5 is a mixture of capryloylglycine, sarcosine and extract of Cinnamon zylanicum, sold by the company SEPPIC, such as those described in International patent application PCT/FR98/01313 filed on Jun. 23, 1998.

Capigel™ 98 is an acrylate copolymer sold by the company SEPPIC.

Lanol™ 2681 is a coconut caprylate/caprate mixture sold by the company SEPPIC.

The invention claimed is:

1. A cosmetic, dermopharmaceutical or pharmaceutical composition, characterized in that said composition comprises an oil phase, an aqueous phase, at least one emulsifier of water-in-oil (W/O) type, at least one emulsifier of oil-in-water (O/W) type, in the form of an inverse latex, said composition comprises from 0.1% to 10% by weight of said inverse latex and said inverse latex comprises from 20% to 60% by weight of a branched or crosslinked anionic polyeletrolyte based on partially or totally salified 2-methyl-2-[(1-oxo-2-propenyl)amino]-1-propanesulfonic acid, copolymerized with acrylamide, the organic solvent constituting the oil phase of said inverse latex comprises isohexadecane.

2. The cosmetic, dermopharmaceutical or pharmaceutical composition as defined in claim 1, characterized in that the anionic polyelectrolyte included in said inverse latex comprises, in molar proportions, from 30% to 50% of the sodium salt or the ammonium salt of 2-methyl-2-[(1-oxo-2-propenyl)amino]-1-propanesulfonic acid and from 50% to 70% acrylamide.

3. The cosmetic, dermopharmaceutical or pharmaceutical composition as defined in claim 1, characterized in that the anionic polyelectrolyte included in said inverse latex is crosslinked and/or branched with a diethylenic or polyethylenic compound in a molar proportion, expressed relative to the monomers, of from 0.005% to 1%.

4. The cosmetic, dermopharmaceutical or pharmaceutical composition as defined in claim 3, in wich the crosslinking agent and/or branching agent of said anionic polyelectrolyte is chosen from ethylene glycol methacrylate, sodium diallyloxyacetate, ethylene glycol diacrylate, diallylurea, trimethylolpropane triacrylate and methylenebis(acrylamide).

5. The cosmetic, dermopharmaceutical or pharmaceutical composition as defined in claim 1, characterized in that said inverse latex contains from 4% to 10% by weight of emulsifiers.

6. The cosmetic, dermopharmaceutical or pharmaceutical composition as defined in claim 1, characterized in that the oil phase of said inverse latex represents from 15% to 40% of the total weight of said inverse latex.

7. The cosmetic, dermopharmaceutical or pharmaceutical composition as defined in claim 1, characterized in that said inverse latex also contains one or more additives chosen especially from complexing agents, transfer agents and chain-limiting agents.

8. The cosmetic, dermopharmaceutical or pharmaceutical composition as defined in claim 1, in the form of a milk, a lotion, a gel, a cream, a soap, a bubble bath, a balm, a shampoo or a conditioner.

9. A method for preparing a cosmetic, dermopharmaceutical or pharmaceutical composition comprising adding an oil phase, an aqueous phase, at least one emulsifier of water-in-oil (W/o) type, at least one emulsifier of oil-in-water (O/W) type, in the form of an inverse latex to said composition, wherein said cosmetic, dermopharmaceutical or pharmaceutical composition comprises from 0.1% to 10% by weight of said inverse latex and said inverse latex comprises from 20% to 60% by weight of a branched or crosslinked anionic polyelectrolyte based on partially or totally salified 2-methyl-2-[(1-oxo-2-propenyl)amino]-1-propanesulfonic acid, copolymerized with acrylamide, the organic solvent constituting the oil phase of said inverse latex comprises isohexadecane.

10. The method as defined in claim 9, wherein said composition is in the form of a milk, a lotion, a gel, a cream, a soap, a bubble bath, a balm, a shampoo or a conditioner.

11. A cosmetic, dermopharmaceutical or pharmaceutical composition, characterized in that said composition comprises an oil phase, an aqueous phase, at least one emulsifier of water-in-oil (W/O) type, at least one emulsifier of oil-in-water (O/W) type, in the form of an inverse latex, said composition comprises from 0.1% to 10% by weight of said inverse latex and said inverse latex comprises from 20% to 60% by weight of a branched or crosslinked anionic polyeletrolyte based on partially or totally salified 2-methyl-2-[(1-oxo-2-propenyl)amino]-1-propanesulfonic acid, copolymerized with acrylamide, the organic solvent constituting the oil phase of said inverse latex consists of isohexadecane.

* * * * *